US011069429B2

(12) United States Patent
Burton

(10) Patent No.: US 11,069,429 B2
(45) Date of Patent: Jul. 20, 2021

(54) MOBILE DATA MANAGEMENT SYSTEM

(71) Applicant: David Burton, Camberwell (AU)

(72) Inventor: David Burton, Camberwell (AU)

( * ) Notice: Subject to any disclaimer, the term of this patent is extended or adjusted under 35 U.S.C. 154(b) by 550 days.

(21) Appl. No.: 15/123,191

(22) PCT Filed: Apr. 23, 2015

(86) PCT No.: PCT/AU2015/000242
§ 371 (c)(1),
(2) Date: Sep. 1, 2016

(87) PCT Pub. No.: WO2015/131242
PCT Pub. Date: Sep. 11, 2015

(65) Prior Publication Data
US 2017/0076057 A1    Mar. 16, 2017

(30) Foreign Application Priority Data
Mar. 6, 2014   (AU) .............................. 2014900755

(51) Int. Cl.
*G16H 10/60* (2018.01)
*G16H 40/67* (2018.01)
(52) U.S. Cl.
CPC ............. *G16H 10/60* (2018.01); *G16H 40/67* (2018.01)
(58) Field of Classification Search
CPC .................................................. G06F 19/3418
See application file for complete search history.

(56) References Cited

U.S. PATENT DOCUMENTS

| 2011/0002223 | A1* | 1/2011 | Gross ...................... H04L 47/10 370/235 |
| 2013/0237775 | A1* | 9/2013 | Gross ................... A61B 5/0205 600/301 |
| 2014/0164611 | A1* | 6/2014 | Molettiere ............ A61B 5/1112 709/224 |

FOREIGN PATENT DOCUMENTS

| GB | 2499986 A | 9/2013 |
| WO | 2014/207624 A2 | 12/2014 |

OTHER PUBLICATIONS

Merriam Webster, "definition of the word 'thereby'" Apr. 24, 2020 (Year: 2020).*

(Continued)

*Primary Examiner* — Angela Nguyen
(74) *Attorney, Agent, or Firm* — Crose Law LLC; Bradley D. Crose

(57) ABSTRACT

A data management arrangement that comprises system(s) enabling monitoring and interconnectivity system resources and configuration parameters to be dynamically adapted to ensure re-defined data prioritisation and associated essential minimal data interconnectivity is maintained during high-dependence or critical data applications which arrangement includes the capability to combine and adapt/adjust online network application services connectivity parameters and configurations, mobile or remote monitoring and/or information and communication technology in accordance to required monitoring criteria, monitoring and interconnectivity conditions, status of monitored individual or object, and/or available resources and conditions associated with said NAS connectivity and/or mobile or remote monitoring and/or ICT systems, in accordance to the application and applicable risk mitigation and high-dependence connectivity monitoring aspect and associated requirements, and the capability to combine mobile monitoring or computing (Continued)

location details with current and/or forecast and/or normal conditions in order to determine travel, health, and other alerts, advice and recommendations.

8 Claims, 9 Drawing Sheets

(56) References Cited

OTHER PUBLICATIONS

Gibbs. M. et al., "The Medical-Grade Network: Helping Transform Healthcare". Cisco Internet Business Solutions Group (IBSG), white paper, 2008.
APT Report on "Machine to Machine Communications Applications and Developments", APT/AWG/REP-42, Sep. 2013, pp. 1-40.
Algaet. M.A. el .al., "A Review on Provisioning Quality of Service of Wireless Telemedicine for E-Health Services", Middle-East Journal of Scientific Research, Jan. 2014, pp. 570 to 572.
Wu, G. et al., "An Adaptive Fault-Tolerant Communications Scheme for Body Sensor Networks," Sensors 2010, pp. 9560 to 9608.
Zhang, Y. et al., "Adaptive service Configuration approach for quality of service management in ubiquitous computing environments", Journal of Zhejiang University SCIENCE A. 2009, vol. 10, No. 7, pp. 964 to 975.

\* cited by examiner

HEALTH CONDITIONS eHEALTH ALERT
SLEEP MON -IVE TREND

ALERT
ASTHMA MONITOR

NO GO ZONE
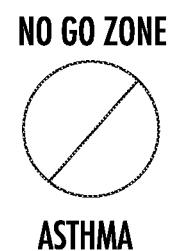
ASTHMA eHEALTH ALERT
SLEEP MON +IVE TREND eHEALTH MONITOR STATUS
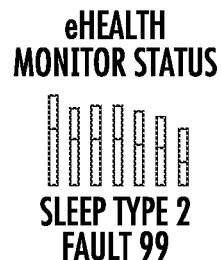
SLEEP TYPE 2 FAULT 99 eHEALTH ALERT
ASTHMA REPORT

WEATHER CONDITIONS

WEATHER ALERT
RAIN & SNOW eHEALTH ALERT
ENV. HAZARD REPORT WEATHER ALERT
RAIN

HAZARD CONDITIONS eHEALTH MONITORALERT
AIR QUALITY

DANGER ASBESTOS

DANGER
RADIATION HAZARD

| HEALTH REPORT INFORMATION; STATUS SETTINGS; ALERTS | |
|---|---|
| ASTHMA MONITORING SYSTEM ALERT | ● |
| AIR POLLUTION ALERT | |
| SMOG ALERT | |
| | |
| | |
| | |

[12]

| HEALTH REPORT MONITORING STATUS SETTINGS; ALERTS | |
|---|---|
| ASTHMA ALERT | ● |
| ASTHMA REPORT REGIONS COVERED | |
| DIABETES | |
| FITNESS | |
| WEIGHT | |
| STRESS | |
| EPILEPSY | |

[13]

| eHEALTHNETWORK USER/PATIENT MEDICAL HISTORY | |
|---|---|
| OSA | MILD ▽ |
| SNORING | SEVERE ▽ |
| INSOMNIA | MILD ▽ |
| ASTHMA | ASTHMA ALERT ▽ |
| HEALTH STATUS | ASTHMA ALERT ▽ |
| SPECIALIST OPT IN | HEALTHBOOK360 ●<br>SLEEPBOOK360 ●<br>REQUEST ASSIST ● |
| GP OPT IN | HEALTHBOOK360 ●<br>SLEEPBOOK360 ●<br>REQUEST ASSIST ● |
| | |
| | |

[14]

| HAZARD REPORT INFORMATION; MOBILE MONITORING STATUS, SETTINGS, ALERTS | |
|---|---|
| ASBESTOS | ● |
| ASTHMA MONITORING SYSTEM STATUS | |
| ASTHMA MONITORING SYSTEM ALERTS | |
| | |
| | |
| | |

[15]

| HAZARD REPORT MOBILE MONITORING, STATUS, SETTINGS, ALERTS | |
|---|---|
| ASTHMA ALERT REPORTS | ● |
| ASTHMA REPORT REGIONS COVERED | ▷ |
| DIABETES | ▷ |
| FITNESS | ▷ |
| WEIGHT | ▷ |
| STRESS | ▷ |
| EPILEPSY | ▷ |

FIG. 7B

MOBILE DATA MANAGEMENT SYSTEM

With the rapid emergence of more demanding mobile online applications, such as eHealth and industrial monitoring applications, a new degree of reliability and data interconnectivity dependability needs to be considered. In particular, connected eHealth mobile-based systems combined with SAAS or Cloud applications must contend with a new and special set of requirements applicable to established minimal standards or expectations applicable to medical diagnostic, monitoring or therapeutic applications. Additionally, in terms of diagnostic monitoring for industry and health applications other factors (enabled via the present invention) such as minimal/optimised and deterministic delay or skew between two or more monitored channels of information, minimal/optimised and deterministic data and information monitoring delays, and/or minimal/optimised variation between changes in monitored clinical signals of interest and remotely relayed measures.

An example of one such eHealth requirement which cannot be compromised during healthcare mobile remote monitoring (for example but not limited to) is the need for medical data and information transfer to be managed in such a manner that traditional mobile computing communication constraints or signal and call dropouts are risk-mitigated in a manner capable of preventing adverse health outcomes at all times.

Accordingly, the present invention provides a data management system which incorporates data management and prioritisation systems applicable to high-dependence or high priority information exchange applicable to health, industrial and even certain consumer electronic fields.

In particular the present invention incorporates high-dependence data management (HDCM) capabilities which enable the resources and configuration parameters associated with any of connectivity system(s), monitoring system(s), mobile-device(s), remote links, and/or network application service (NAS) to be dynamically adapted in accordance to monitoring conditions and monitored conditions applicable to required resources and data prioritisation needs at any particular point in time. The present invention can enable adjustment of an array of system configurations covering online, offline, local, remote-linked site(s), remote monitoring, across NAS and or mobile monitoring and/or mobile ICT systems. communication and/or biofeedback and remote monitoring (NAS) aspects of monitored parameters (i.e. physiological and/or industrial and/or other "things") monitoring device parameters, mobile phone/computer parameters, monitoring system view parameters, monitoring system review parameters, monitoring system storage parameters and system roles along with configuration capabilities including monitoring study format(s), data response(s), data interconnectivity format(s), data buffer(s), data acquisition(s), and signal preamplifier(s).

The embodiment example of the present invention includes independent NAS such as eHealthNAS which can provide a range of services applicable to eHealth. One such service is GOTOeHealth which seamlessly manages the HDCM systems management functions during any eHealth communication links which are operated to manage not only superficial or thin-footprint data streams such as the current Personally Controlled Electronic Health Record (PCEHR) example in Australia, but also a comprehensive clinical data aspect which general practitioners and medical specialists tend to require in terms of providing patients meaningful health management, advice or diagnosis.

In other-words the present invention enables data communications, graphic user interface, application functions, data management, data communication, and other aspects within a software as a service (SAAS) or other application in order to minimise or avoid jeopardising the diagnostic, interpretation(s), therapy, control or other healthcare aspects associated with a mobile device connected or application-based medical, scientific, industrial or other monitoring.

Accordingly, the present invention provides enhanced data management capabilities capable of enabling more deterministic, controlled and/or appropriately managed data transfer in order to mitigate the risk and manage circumstances where misdiagnosis or misleading measures or health status indications could otherwise jeopardise patient or consumer user health outcomes.

The present invention's SAAS deployment option incorporates a system whereby a SAAS-integrated or SAAS-independent "HDCM-watchdog" or surveillance function continuously tracks the update status of various data types as well as associated data priorities during mobile connected-device monitoring applications. In particular, continuous tracking of displayed, stored, and reviewed numeric, tabular, graphic, informational, warning or alert displays and indicators, and other data types are tracked in terms of data delays, data delay variations, multiple data channel miss-alignment (offset), data synchronisation, lost or corrupt data packets, trends and/or other unacceptable circumstances.

These said unacceptable circumstances or predicted upcoming critical-data issues can be detected and managed in accordance to predetermined (or preconfigured) system requirements. In this way available data-bandwidth and various data-communication channels and/or different mediums (cellular network, optical network, Wi-Fi, blue-tooth, satellite, Wan LAN, etc.) can be utilised in a manner designed to ensure critical data, system warnings and alerts, crucial to health outcomes are appropriately prioritised and adapted to the interconnectivity and monitoring circumstances. Appropriate management refers to providing a means to adapt and configure graphic user interface indicators and control options, various monitoring and communication system(s) system performance and resources, monitoring system configuration and system resources, and also data communications performance, resources and data-prioritisation according to minimal criteria designed to minimise health risks.

However, the present invention can notify the user that the numeric display and warnings are being maintained with minimal delay both locally and with any associated remote control monitoring centre, during temporary communication delay conditions. In this way vital data measurements such as heart-rate, respiration rate, oxygen saturation, blood-pressure, temperature and the like can be both preserved during the most severe data communication conditions, as well as flag early intervention or assistance should this be warranted based on the subject's health status and the deterioration in eHealth monitoring conditions. In order to preserve data-bandwidth allocation for the most critical monitoring aspects during compromised interconnectivity conditions, optional monitoring aspects such as real-time waveform displays can be configured as secondary tasks. These secondary tasks could be suspended in order to preserve the system operational and/or data communications bandwidth capabilities for the most critical tasks in the first place.

In another example of the present invention there could be critical monitoring condition alert generated in circumstances where a mobile device and/or monitoring system's memory or other system resources are approaching maximum capacity or critical levels. In these circumstances the present invention can automatically and seamlessly activate a secondary on-board or off-board mobile-device memory backup system, such as a wire or wireless connected memory storage (or "HDCM-watchdog") system.

The present invention can be configured (including deployment of "watchdog" function) so that once data communications issues or system operational factors, such as processing power memory, have been restored, the back-logged data which has been buffered during any periods of communication or system resource constraints can be streamed to a required or designated site such as a remote monitoring control room or application, in order to maximise data integrity and data monitoring continuity.

Additionally in another mode the present invention (for example only), can stream emergency data status or system alerts via SMS or other emergency or backup connectivity channels. Moreover, with the possibility of dynamic linking to main patient monitoring application versus the said emergency or backup communication channels can be accessed via monitoring view, review or analysis applications in order to enable data sets to be flagged, system user (s) alerted and reconstituted to overcome data misalignments, delays, errors or other compromised data circumstances.

Background: Health monitoring in general and specifically as it applies to clinical data representative of physiological measures or conditions is often extremely dependent on factors such as the reliability of data interconnectivity and the responsiveness of data measures and indices to accurately reflect the monitored subject's health status in a precise and unambiguous manner. In particular, the monitoring must provide information representative of the health outcomes of an individual. Importantly, such monitoring should not inadvertently introduce complexity or risks which can ultimately confound or delay an individual's diagnosis due to added confusion, ambiguity. In general, the veracity of a local or remote monitoring system can contribute to the health but also adverse health sequelae of a monitored individual.

For example, in the case of anaesthesia consciousness depth monitoring ((PCT/AU2010/001050; 2009) the physiological data and also associated indices are highly susceptible to factors such as online responsiveness and the latency of the measurement outcomes. These delay and measurement responsiveness aspects are critical to remote monitoring and particularly as it relates to eHealth and other mobile based monitoring services and applications.

DESCRIPTION OF THE INVENTION

The Dynamically adaptive high-dependence connectivity management (HDCM) system enables a range of system configurations, system performance tracking system(s) covering crucial monitoring and interconnectivity requirements, along with means to provide adaptive control in a pre-emptive system control interventional manner capable of ultimately averting avoidable risk scenarios, applicable to conventional mobile phone or computing connectivity network application services, remote monitoring and other circumstances or conditions.

In particular, the present HDCM system incorporates the means to automatically or manually establish acceptable monitoring criteria in order to continuously track and detect potential risks or deviations from these said criteria. Such high-dependence connectivity conditions can include (for example but not limited to) safe-operating margins, thresholds and ranges as well as the determination of confidence levels based on appropriate computational methods designed to predict the probability or likelihood of upcoming data connectivity concerns which can or are violating minimal acceptable monitoring conditions.

The present HDCM system can be deployed to augment conventional mobile phone and computing technology network application services (NAS) in a manner where more crucial monitoring such as eHealth, industrial, certain consumer applications, and other applications where high-dependence and/or deterministic data interconnectivity is important or essential.

The present HDCM system comprises of any of the following aspects:

Connectivity Configuration and Connectivity Management Systems

The HDCM system enables configuration criteria and setup parameters across a range of parameters essential to high-dependence data interconnectivity monitoring and applications, The HDCM system enables more than one primary and secondary (backup) data communications channels, along with the means of utilising more than one communication medium as a backup or secondary communication system, such as (but not limited to) satellite connections is rural regions where conventional communication networks can prove to be unreliable.

The HDCM system can be configured to accommodate different levels of data prioritisation. Different monitored channels of data can be assigned different degrees of important and data prioritisation in accordance to the critical nature of each data channel. Additionally, derived indices or measures, such as heart rate variability, heart rate or cardiac events can be prioritised in terms of data communication bandwidth in a manner whereby essential information applicable to determining an individual's vital signs can be transmitted in preference to less (but significantly higher bandwidth demanding data). For example, rather than delay or risk the transmission of heart measures, rate variability or the incident cardiac events, the present invention has the online processing capability to mediate lower bandwidth but higher important indices, as described, versus higher-bandwidth but lower priority ECG (raw cardiac signal data), in order to preserve the available interconnection for the most critical information. Such critical data and prioritisation can be fully configured by the system users and/or NAS provider.

This data band-width allocation, mediation, facilitation and prioritisation, coupled with data-ranking (importance), data type (raw data versus derived vital measure or signs) enables a unique and comprehensive NAS management method or device which can covert/upgrade expensive existent or conventional communications infrastructure into useful and reliable information and communications systems for high-dependence applications, including those of the health and industrial sectors.

HDCMS can be configured in an efficient user-interface manner whereby the data bandwidth allocation of one or more interconnectivity formations (SMS, optical network, copper network, Wi-Fi, Bluetooth, pager alerts, automatic phone alerts, etc.) can be segmented into emergency or high-dependence low-data bandwidth channels such as numeric blood-pressure, heart-rate, heart-rate variability, oxygen-saturation, C02 levels, respiration rates, temperature and the like can be segmented and not be overwhelmed (band-width-wise)

from lower priority but higher bandwidth data (such as video, audio, or high sample rate physiological data.

Online connectivity latency (delay), latency variability, true-time-synchronisation (alignment with actual time synchronisation and data time-alignment as well with other channels of information) real time characteristics of data relating to one or more monitored channels with one or more data types (i.e. physiological data, video, audio, sensor/transducer measures, etc.) along with other parameters such as Monitoring, Acquisition and Signal Processing, Transducer Time Delay Factors, Measurement System Time Delay Factors, Data Acquisition Time Delay Factors, Alarm, Warning and other Notification Time Delay Factors as listed here can be configured dynamically in order to adapt to changing and/or compromised information and communication links as part of the present inventions HDCM capabilities.

Monitoring, Acquisition and Signal Processing
Monitoring device type, requirements and configuration.
Sensor types, requirements and configuration.
Signal Preamplifier criteria and setup parameters.
Digital Signal Processing criteria and setup parameters.
Filtering criteria and setup parameters.
Compression criteria and setup parameters.
Data acquisition criteria and setup parameters.
Transducer Time Delay Factors
The Transducer to measurement time delay (time delay between physiological signal change and measurement)
Transducer to measurement time delay (time delay between physiological signal change and measurement) data time delay variance
Measurement System Time Delay Factors
Measurement to local display indicator data time delay
Measurement to local display indicator data time delay variability and variance
Measurement to remote display indicator data time delay
Measurement to remote display indicator data time delay variability or variance
Data Acquisition Time Delay Factors
Measurement to local acquisition data time delay
Measurement to local acquisition data time delay variability or variance
Measurement to remote acquisition data time delay
Measurement to remote acquisition data time delay variability or variance
Alarm, Warning and other Notification Time Delay Factors
Measurement to local alarm, warning or other notification data time delay
Measurement to local alarm, warning or other notification of data time delay or data delay variability
Measurement to remote alarm, warning or other notification data time delay
Measurement to remote alarm, warning or other notification data time delay variability or variance
Online Critical Interconnectivity Surveillance System The purpose of the HDCM system is to predict and avert connectivity issues or risks in advance so that preventable or predictable data failures can be avoided while unavoidable issues can be managed with backup systems or prompt intervention where required or appropriate.

For example, the present invention provides clinicians or health workers data latency or data alignment/synchronisation assurance and data control/management in cases where more than one channel information require time alignment between said data channels, and such provisions are warranted. Such "data control/management" ensures that the time delays or readings of data including vital signed has been examined in advance in terms of minimally acceptable criteria and the recipients of this data or such measures have the confidence and assurance that the data has been tracked or pre-screened in terms of crucial aspects such as the synchronisation between different data channels or different information mediums (i.e. physiological, video, and/or audio data). The said "tracked or pre-screened information" refers to analysing data communications or transfer in accordance to previously determined criteria (such as but not limited) described elsewhere (per heading "MONITORING SYSTEM CONFIGURATION" sections 1 to 6).

For example, electrocardiogram, blood pressure and heart rate readings need to be updated at minimally acceptable intervals, must have minimal and predefined delays between a user/patient being monitored and the reception of such information. Additionally, the stability and status factors must be both available for the system users but also linked to alarms. These configurations, alerts, alarms and other system criteria and parameters can be only be configured by the appropriate authorised system users (roles)

PRIOR ART

The integrity of data, the time alignment and stability (variation/predictability) or synchronisation between different channels or types of data, and also the time delays and stability (variation/predictability) associated with monitoring physiological or psychological states of biologic objects or individuals present important challenges.

These challenges are further exasperated as more sophisticated and less direct communication approaches continue to emerge. While the distinct advantage of more sophisticated computing systems such as cloud computing are characterised by ease and simplicity of use, this very characteristic can present risks when it comes to critical data connectivity (such as but not limited to) eHealth monitoring applications where clinical data (including vital signs) timing integrity can be crucial.

For example, if a patient in an ambulance is being remotely monitored then the time between two heart beats can be crucial in terms of averting or supervising an individual who may be at risk of cardiac arrest. Moreover, while disconnection or interruptions can be tolerated during conventional mobile telephone conversations, the same cannot be said when it comes to high-dependence medical data interconnectivity.

The present invention addresses these factors by incorporating 3 unique network application service (NAS) functions designed to improve the reliability of critical data interconnectivity situations, applicable to applications such as medical data interconnectivity.

Industrial Online Surveillance Embodiment Example of the Present Invention

In one deployment example of the present invention a remote monitoring capability incorporating a means of monitoring systems (objects/devices) for the purpose of sensing and then providing local or remote monitoring (via the internal or other communication methods) of sensors or transducers or other interfaces to the circuits or mechanical parts of said monitored "systems" in order to enable early signs of pending risks, issues or even disasters. By enabling remote monitoring of moving parts or circuits that are subject to wear and tear or other causes of failures from time to time, a degree of enhanced and automated safety assurance to the system users of people involved with the systems can be provided. For example, embedded sensors such as speakers or microphones can be used to detect exceptional or extraordinary frequencies or sounds representative of worn mechanical bearings, loose or vibrating parts and the like. In another example a vibration, microphone or other sensor type can enable spectral and general vibration and acoustic analysis of a system in order to detect problematic bearings or other mechanical defects before such defects lead to higher risk scenarios. In one example, a humidity chamber that needs to be regularly replaced due to hygiene factors may be analysed in terms of a unique read only memory (ROM), embedded proximity sensor, embedded chip, laser etching, barcode scanning mechanism, or other identification means in order to determine the usage in terms of time and wear-and tear of a humidity chamber. This determination can prevent excessive wear which can potentially aggravate system leakage risks or infection risks to the user, for example.

Other examples include the deployment of electronic or computer intelligence designed to assess the performance of systems at appropriate intervals and times so that factors such as blocked or dysfunctional air-filters that are impeding the safety, hygiene or performance of breathing assist devices can be examined via a number of approaches in order to seamlessly advise users of maintenance or service issues and requirements. For example, the pressure drop across a filter chamber or the extra load confronted by a motor controlling a breathing-assist device can contribute to the diagnosis of a required filter change. This diagnosis could effectively deploy the present inventions remote monitoring capabilities combined with ICT and automated computational capabilities to send the user of the breathing-assist device an automatic SMS or cell-phone, or email or other reminder of the diagnosed issue and likely and actual cause and remedy. Moreover, this type of function enables suppliers of such devices or for that matter industrial and medical system is general, to automatically dispatch a service function or representative to correct the diagnosed defect. It is also possible to even automatically dispatch required part or consumer replacement stem direct to the user's selected destination for immediate changeover. Additionally, the system demonstrating a defect or potential risk can itself alert the user or even undertake immediate or interim remedial action designed to minimise the related risks to the system user or associated system. Any combination of these types of fully automated remote monitoring capabilities will enable a level of efficiency and automation that ultimately reduces patient and consumer costs and introduces a level of efficient competitiveness that surpasses conventional approaches.

Any unique combination of these properties along with the use of the eHealthATLAS and/or eHealthNAS and/or GOTOeHealth and/or in general the overall HDCM systems unique methods and apparatus variants contribute to providing greatly enhanced mobile monitoring systems and capabilities for industrial, medical, health and other applications where ICT integrity, determination and HDCM factors are a consideration.

Additionally, remote maintenance monitoring including sensing via Internal existent sensors such speaker, microphone, motor, filter chamber, airflow, air-pressure "sensors";
- whereby said "sensors" can sense noise, pressure, airflow, sound, vibration, voltages, current, magnetic and other states or changes in terms of normal operating versus abnormal "levels or combinations of levels";
- where said "levels or combinations of levels" can be analysed in terms of possibilities and probabilities related to potential upcoming or existent fault conditions as a means of "predictive and preventative fault and safe operational analysis";
- where said "predictive and preventative fault and safe operational analysis" can be deployed as a means of determining user advice;
- where said "predictive and preventative fault and safe operational analysis" can be deployed as a means of determining user spare part or consumable requirements;
- where said "predictive and preventative fault and safe operational analysis" can be deployed as a means of automatically supplying user consumable requirements;
- where said "predictive and preventative fault and safe operational analysis" can be deployed as a means of automatically supplying user reporting and/or consumable requirements and/or specific device and circumstance user instructions;
- where remote maintenance monitoring including pressure and system including go measure supply rails, pressure sequences etc.

DESCRIPTION OF THE INVENTION

Online Mobile-Monitoring Map-Linked Health-Tracking Including Integral Environment and Hazard Monitoring & Environment Conditions The present invention's context health analysis can compare a monitored individual's current health status as it relates to:

a) personalised database containing references to acceptable or normal health status measures or derived measures including physiological measures, indices and other numeric, tabular or graphic health status outcomes.

b) population database containing a specifically-defined or general population group's health status and physiological measures, safe or normal operational thresholds and/or ranges, or derived measures including physiological measures, indices and other numeric, tabular or graphic health condition of status outcomes.

c) consumer/patient medical history with the provision for pre-determines safe-functional ranges and thresholds for physiological outcomes measures or derivations Additionally, the present invention can compute for a predetermined or selectable period of time of study (i.e. this being the desired or selected investigational period, such as the sleep period, a gym exercise period, work-period, a training period, a business meeting or other period of time of interest in terms for health assessment) range of selectable or automatically activated Secondary Physiological-related Data or Primary Physiological-related Data.

Additionally, the present invention can simultaneously monitor and analyse environmental measures.

These said health measures can be monitored, while the monitored physiological and/or environmental parameters are compared to safe-margins or normal margins of "physiological mechanisms or associated functional outcomes" (heart, sleep/wake, asthma breathing volume and/or effort measures, sleep structure, fragmentation, sleep efficiency. AHI, RDI, AHI, RERA sleep hypnogram and other "sleep measures", "health parameters" or "respiratory parameters" etc.).

In this way the present invention can "determine" whether negative or concerning trends occur in terms of health status as well as whether these said trends can be correlated with factors such as environmental conditions (ie pollens, gases, pollution, temperature, light conditions, surrounding sound etc.). These said "determinations" can then be referenced in order to pre-empt potential or onset of undesirable health conditions in order to potentially "avert such conditions" or deploy various forms of "early health warnings or interventions".

One such embodiment of the present invention (but not limited to) can include the tracking includes of both functional states and context of said sates, during an individual's sleep and/or wake periods. Said "context "analysis" can incorporate information relating to sleep structure, fragmentation, sleep efficiency. AHI, RDI, AHI, RERA sleep hypnogram and other "sleep measures", "health parameters" or "respiratory parameters" in order to determine existent or the inset of or the potential onset of potential adverse sleep, breathing or other health conditions applicable to adverse health conditions.

Moreover the present invention can predict the likely sleep outcomes such as sleep efficiency and other sleep quality measures based on this "normalised" or "personalised" data base reference in order to provide a means for said individual to gauge their sleep and general health progress.

Moreover, using the present inventions capacity to compare synchronisation between environmental versus physiological signals, measures, indices and sleep hypnogram enable the present invention to predict potential causes of sleep and/or respiratory and/or other health disturbances or conditions.

For example, a correlation between sound monitoring of the said mobile system and sleep fragmentation can advise individual of sound related arousals, disturbances or arousals. Moreover the individual or remote monitoring site can elect to replay disturbance event providing a means (for example but not limited to) associating sleep disturbances with source of excessive sound disturbance. (i.e. snoring partner, chiming clock, street noises, slamming doors, household sound disturbances or vibration etc.). In this way not only can sleep fragmentation or disturbances be detected but such information can enable diagnosis of insomnia, sleep disordered breathing and other adverse health conditions.

Similarly, the present invention can correlate other environmental conditions such as temperature and humidity with physiological conditions such as temperature, heart rate, sleep fragmentation and/or arousals and/or sleep architecture disruption in order to determine or predict source of sleep or other health adverse events of conditions.

In this way the present invention can for the first time not only monitor sleep and/or other health conditions but also advice user of potential and likely causes of sleep or other adverse health states, at any time during sleep or wake periods. Accordingly, the present invention can "advise" monitored individual how to optimise sleep and mitigate an otherwise restless night, which in turn can potentially mitigate a failed meeting event, unproductive day or even tragic incident.

One object of the present invention is "noise cancellation earplugs or other hearing attenuation approaches designed to (for example but not limited to) allow conventional speech but block or attenuate snoring and other unwanted sounds, such as snoring in the same room as a sleep individual. The said "unwanted" sounds or snoring can be distinguished with the assistance of the syntonisation approached described herein.

Another object of the present invention is to enable, for example, environmental conditions such as temperature and heating to be adjusted in accordance to an individual's requirements in order to achieve optimal sleeping conditions (predetermined or dynamically computed from monitored environmental and physiological conditions, for example).

The said "controls" (such as referred to in the attached figures) can include room temperature and/or humidity thermostat settings.

These said "controls" can also include bed positioning or adjustment device designed to minimise snoring.

The said "controls" can include patient positioning training device such as a patient worn vibration or inflatable device designed to guide, prompt or coach monitored individual to adopt a change in sleeping position in order to minimise snoring conditions.

The objective(s) of the present invention is to provide or enable an apparatus and method enabling any combination of connected mobile monitoring systems ("mHealth"), user/consumer/patient worn device or system, software as a service (SAAS), cloud and other network application and services (NAS) systems,
  mobile-monitoring of one or more channels of "health"/physiological information,
  general "health" report/information data,
  user/consumer/patient-specific "health" report/information,
  mobile-monitoring of one or more channels of environmental condition information,—
  mobile-monitored environmental condition information including (but not limited to) weather conditions,
  report/information relating to environmental condition information including (but not limited to) weather conditions,
  mobile-monitored information relating to environmental hazard conditions information including (but not limited to) gas, allergy, pollen, smog, asthma and other actual or potential current or emerging hazard conditions,
  report/information relating to environmental hazard conditions information including (but not limited to) pollen risk information, air-quality or pollution risk information, traffic congestion information, traffic congestion and/or fumes information, gas hazard, allergy hazard, smog hazard, asthmatic hazard and other actual or potential current or emerging hazard conditions,
  "locational data and or directional data" to be overlays or combined with both predictive or trend-data outcomes as it relates to current patient/consumer mobile or non-mobile communication and/or computer system, in order to visualise or alert with any other communication approach, display or notification methods patient/consumer of pending concerns which could potentially be averted or minimised,
  information/report on normal and/or safe-operating and/or safe margins of functional physiological performance or conditions) comparative "health" information or comparative report/information,
  user/consumer/patient-specific information/report on normal and/or safe-operating and/or safe margins of functional physiological performance or conditions) comparative "health" information or comparative information,
  general or non-user/consumer/patient-specific information/report on normal and/or safe-operating and/or safe margins of functional physiological performance or conditions) comparative "health information or comparative information, user/consumer/patient-specific information/report on normal and/or safe-operating and/or safe margins of functional physiological performance or conditions) comparative environmental weather information or comparative information, general or non-user/consumer/patient-specific information/report on normal and/or safe-operating and/or safe margins of functional physiological performance or conditions) comparative environmental weather information or comparative information, user/consumer/patient-specific information/report on normal and/or safe-operating and/or safe margins of functional physiological performance or conditions) comparative environmental hazard information or comparative information, general or non-user/consumer/patient-specific information/report on normal and/or safe-operating and/or safe margins of functional physiological performance or conditions) comparative environmental hazard information or comparative information, "processing and/or presentation capability to associate/correlate" any combination of the said information sources in terms of determining actual and/or potential and/or trended and/or trending and/or predicted "health" status risk or other "health" status functional aspects, control and/or feedback and/or biofeedback and/or servo control and/or other control means of referencing information outcomes of said "processing and/or presentation capability" in to associate/correlate" in order to control directly or indirectly or influence any device or method, whereby said control can (but is not limited to) averting or minimising an actual or potential "health" risk, display of communication or "presentation capability" and/or feedback and/or biofeedback and/or servo control and/or other control means of referencing information outcomes of said "processing and/or presentation capability" in to associate/correlate" in order to control directly or indirectly or influence any device or method, whereby said control can (but is not limited to) averting or minimising an actual or potential"health" risk, Whereby said "presentation capability" includes any of display and/or alarm and/or alert and/or notification and/or communication and/or storage and/or other information presentation or interface means.

Whereby "locational data and or directional data" can be derived from one or more sources such as (but not limited to) any combination/hybrid/overlay of satellite data, video data, camera data, atlas data, navigator mapping system data, map data in general, topographic landscape data, street-scape data or other means of presenting "locational and/or directional" data associated with any location or direction in the world. Said locational data can include (but is not limited to) information directly related to or derived from global positioning system (GPS) information sources.

Whereby "health" information/reports or monitored information can include (but is not limited to):health warning; allergy warning; pollen no-go-zone; air quality warning; no-go-zone; no go zone asthma; no go zone asthmatics; no-go-zone allergy sufferers; no-go-zone allergy; no-go-zone pollution, no-go-zone smog, no-go-zone fumes, no-go-zone air quality; no-go-zone smoke; no-go-zone carbon monoxide; no-go-zone toxic gas; no-go-zone EMF levels; no-go-zone radiation; no-go-zone chemicals; no-go-zone toxicity; etc.

Whereby "environmental weather" information/reports or monitored information can include (but are not limited to)—high temperature warning; low temperature warning; high humidity warning; low humidity warning; rain warning; fire condition warning; fog warning; driving visibility warning; allergy warning; pollen no-go-zone; air quality warning; no-go-zone; no go zone asthma; no go zone asthmatics; no-go-zone allergy sufferers; no-go-zone allergy; no-go-zone pollution, no-go-zone smog, no-go-zone air quality; no-go-zone smoke; no-go-zone toxic gas; no-go-zone EMF levels; no-go-zone radiation; no-go-zone chemicals; no-go-zone toxicity; etc.

Whereby "environmental hazard" information/reports or monitored information can include (but is not limited to)—pollen no-go-zone; air quality warning; no-go-zone; no go zone asthma; no go zone asthmatics; no-go-zone allergy sufferers; no-go-zone allergy; no-go-zone pollution, no-go-zone smog, no-go-zone air quality; no-go-zone smoke; no-go-zone toxic gas; no-go-zone EMF levels; no-go-zone radiation; no-go-zone chemicals; no-go-zone toxicity; no-go-zone fumes, no-go-zone carbon monoxide; no-go-zone asbestos; no-go-zone toxic chemical; no-go-zone pipes; no-go-zone cables; no-go-zone gas pipes; no-go-zone electrical power station; no-go-zone electrical radiation; no-go-zone EMF; no-go-zone radio frequency; no-go-zone radiation; no-go-zone fire; etc.

Whereby a number of "health", "environmental weather" and "environmental hazard" categories are repeated, combined or overlap in order to accommodate for cross-over considerations such as (but not limited to predicting and/or trending and/or emerging risks or conditions whereby combined conditions such wind leading to moving-air pollutants (gas, smoke, smog, allergies, pollens etc.) can be taken into account in terms of changing conditions and risk health analysis.

Whereby "locational data and or directional data" can include travel routing or trip information in order to potentially avert any travels to our through regions of "health", "environmental weather", and/or "environmental hazard" concerns or emerging issues;

Glossary/Object of the Present Invention

Informational data—including but not limited to mobile physiological related monitoring, GPS communication system data, GPS location data, software as a service (SAAS), cloud software service data, search engine data, or online or web-based data, or network or communication or interface data of any type.

Connected system or connected mobile system—refers to "connection" with any wire or wireless system/network/interface, point to point communication system/network/interface, point to many point communication system/network/interface, many point to many point communication system/network/interface.

Geographical location—Any data which contributes to the partial or complete determination of an object in space, or location anywhere in the world.

Time synchronised—refers to the alignment of one or more data streams or sets of data with another data stream or set of data.

The alignment of an ECG physiological signal with the pulse waveform can be indicative of the pulse transient time measure and therefore the "time synchronised" nature of this ECG and pulse waveform and data is critical.

The alignment of the video of a subject with the simultaneously monitored EEG data can be indicative of an EEG-related seizure and therefore the "time synchronised" nature of this video and EEG data is critical.

The "time synchronised" nature of the alignment between breathing sounds, and breathing movements, breathing associated or derived signals during sleep (for example but not limited to) could be indicative of sleep disordered breathing. However, failure of such a "time synchronised" relationship between say breathing signals and sounds monitored during sleep could also be important information, as in the case where such a misalignment of data could be indicative of different individuals associated with breathing signal measures and monitored sounds, as in the case of a snoring bed-partner, for example. Determination and analysis of signal synchronisation and associations with other signals enables a more sophisticated and accurate approach tracking breathing sounds in general or more specific snoring, wheezing, caught and other events of potential interest. Moreover, when there are other patients or people in a similar breathing proximity and other sound recording can be ambiguous in terms of associating the actual person with the sounds recorded. Consequently, the ability to distinguish the sources of recorded or monitored sounds can be an extremely useful function, and particularly as it applies to mobile monitoring applications.

The "time synchronised" nature of alignment between sounds recorded during sleep and primary physiological data (such as EEG arousals) and/or secondary physiological data (such as sleep hypnogram architectural changes or sleep stage changes) could also present highly important information. For example, if an individual awakens during the night and wishes to utilise the present inventions sleep disruption related event (SDER) causation determination or suggestion automatically presented (such as last suspicious awakening selectable mobile monitoring event selections), then monitored sounds synchronised to predetermined physiological events of interest (such as but not limited to arousals, sleep fragmentation, changes in sleep architecture, blood-pressure changes, pulse changes or other) may be highly relevant is assisting an insomniac in the task of tracking down causations or his sleep disruptions. Ie one SDER event could be the chiming of a clock recorded in conjunction with the related sleep disruption such as a change in sleep stage or arousal. Moreover, activation of the SDER causation could reveal the actual monitored sound of the clock chime and reveal a hyper-sensitivity to sounds during sleep as one possible insomnia causation. Similar relationships could potentially be identified as it related to room temperature, room lights, street sounds, other environmental factors or physiological temperature or other physiological parameters.

Additionally, an important object of the present invention is the capability to control and validate the time synchronisation between different data channels but also as it relates to interrelationships between different physiological signals or events. For example, determination of the synchronisation (alignment/correlation/association) between awakening arousal events, or micro arousals or arousals of any kind with external and physiological events can provide useful information, such as the causation and prevention of events or adverse health sequelae.

Similarly, simultaneous monitoring and accurate synchronisation of these signals during monitoring of an individual can provide important information, such as the causation or symptoms relating to and prevention of epilepsy seizures (for example only).

Online software or communication interface via wire and/or wireless and/or EMF data interconnectivity means—includes but is not limited to any combination of web data or information or programming step(s), online software or information or programming step(s), software as a service (SAAS) online web data or information or programming step(s), so-called cloud computer service or application, network communication or data system, point to point communication or data system, point to many point communication or data system, many point to point communication or data system.

GPS related data—refers to data derived from or contained within GPS communication interconnection or related data information streams.

Other environmental Data or Conditions information—Refers to any online or offline source or information repository including but not limited to GPS, GPS related data, online or offline software or communication interface via wire and/or wireless and/or EMF data interconnectivity means, connected system or connected mobile system, Informational data or other available memory/information/data source.

Unique Aspect of the Present eHealthATLAS Invention

Method and process whereby health, weather, hazard and other environmental conditions can be tracked in terms of patient/user mobile monitoring, trending, alerts, status and/or normative health databases and other information sources Normative Databases of standard or normal health, weather, hazard and other environmental conditions as well as current conditions, traffic reports an the like can be manually or automatically updated to provide both up to date reports on current or forecast conditions, but also enable comparison with normative data-base to establish important or relevant alerts, warnings, alarms, along with safe-margin determination & associated trend, alerts and alarms Map-linked views capable of associating health monitoring conditions or trends with environmental factors such as pollens, air-pollution or allergies Health-linked navigational aids capable of health-conscious-routing (i.e. avoiding polluted areas or pollen alerts for asthmatics)

Early interventional health tips or hints such as tracking a child's activity versus temperature versus location (for the prediction of potential asthma onset risk factors based on combinations and trends in terms of monitored breathing, weather conditions, such as excessive heat or humidity, environmental hazards (like pollution) and locational activity factors . . . , and other environmental, activity, health or general risk conditions. Early interventional health tips/hints & control (servo, feedback, biofeedback, "internet or things/objects"—i.e. compensation for factors such as environmental pollution by activating vehicle or household air-filtering and air-conditioning. Parents tracking risks to avoid (for example) serious asthma onset with a vulnerable child could be assist via mobile tracking applications designed to analyses and correlate factors in order to identify potential excessive risk scenarios. For example, a child who has been just been monitored via a mobile spirometer to exhibit restrictive breathing, combined with high temperature measures and locational GPS sports center data, could flag a risk for a child or carer who can then potentially provide early interventional guidance or assistance where appropriate, in order to minimize health risks. Similarly, a child with respiratory dysfunction such as asthma could be alerted to use a breathing mask or take their Ventolin as a backup in circumstances where, for example, smog or pollution alert or online monitoring warrants these considerations.

Control/servo interface (including but not limited to "internet or things" or "objects") and/or feedback (including but not limited to PLL, biofeedback) servo) for measures (health monitoring, weather, environment) with automatic countermeasures using internet of things including track said conditions and automatically compensate for factors such as environmental pollution by activating vehicle or household air-filtering and air-conditioning Biofeedback such as neurology and/or ERs along with associated state determination (relaxation, wake, sleep, alert, anxiety) brain mobile monitoring with and/or mobile stress monitoring (heart, pulse, HRV, plethysmography oximetry, temperature, galvanic skin-resistance, movement, activity, position etc.) integrated to control functions such as massage chair or mood/surround music and the like Health root mean cause analysis including (for example) sources of insomnia or awakening events which can be associated with environmental disturbances or changes (excessive noise levels or temperature) along with replay of time synchronized monitored physiology and environmental conditions (i.e. recording of excessive street noise synchronized to awakening/arousal or sleep fragmentation or event)—automatic countermeasures can include temperature adjustment or closing of curtains to reduce noise, for example.

Healthbook360—enabling the personalized health-network with user/patient capabilities to manage GP, specialist, and other intervention or healthcare support with automated health-insurance and government reimbursement and billing considerations. Personalized health-group opt-in capabilities and invites enabling seamless online health group consultations, support, referrals, 24-7 after hours doctor on call services, GP Skype-consultation services via your trusted group of healthcare care-worker, confidants, professionals & experts

PRIOR STATE OF THE ART PROBLEMS

Problem: Conventional mobile-phone communications are primarily designed for general or social communications. Hence, it is not uncommon to find that a call's reception drops out. or is inadvertently disconnected during poor reception or changes in call interconnectivity conditions. Such inconveniences can be customary during personal or business communications, and the usual course is to reactivate call or to have call automatically reactivated. However, during more critical high-dependent data interconnectivity applications, such as health monitoring or diagnostic applications, can result in serious and event fatal consequences.

DESCRIPTION OF THE INVENTION

Solution: In the case of interconnectivity challenges the present invention can detect and pre-empt crucial system issues, along with generating associated status alerts such as the detection of "data bandwidth or communication restrictions". These system messages can still be transmitted via a secondary or backup channel (such as HDCM-watchdog system) as part of an eHealth patient monitoring application. In this way high-risk interconnectivity scenarios can be clearly indicated to system users, in order to avoid mistaken or ambiguous scenarios during delayed, disconnected, suspended, or lost data packets.

The present invention in contrast, incorporates a secondary or supplementary communication channels designed to provide ongoing and uninterrupted data delay surveillance and system alert capabilities of predicting, detecting, and preventing such circumstances.

Problem: in the case of conventional mobile NAS, poor mobile phone reception or data bandwidth restrictions (for example) due to excessive communication demands, monitoring conditions or interconnectivity conditions such as during circumstances where data traffic demands exceed available bandwidth, data transmission and subsequent critical data measurement delays or can be experienced.

In critical monitoring cases using conventional mobile systems or NAS, critical monitoring circumstances such as periods when an individual is being monitored remotely for cardiac palpitations or arrhythmias, can be delayed, interrupted, disconnected or suspended. These communication disturbances can subsequently lead to ambiguous, delayed or mistaken diagnosis. Consequential delays in medical assistance or intervention by ambulance or paramedics workers (for example) can result in high risk or dangerous adverse health outcomes.

DESCRIPTION OF THE INVENTION

Solution: In contrast the present invention's SAAS-connectivity-surveillance system can, in circumstances where crucial data is disrupted, still enable essential information such as arrhythmia measurements. This can be achieved by the present invention detecting or pre-empting or detecting data interconnectivity issues. Such interconnectivity issues can include failures to meet pre-determined minimal criteria requirements, such as ensuring at least heart-rate, blood pressure and cardiac events cardiac palpitations or arrhythmias are continuously updated and displayed.

The said prediction of upcoming data limitations can be evaluated by way or analysing data bandwidth demands, data errors, data delays, data delay variances and comparing these conditions to minimal criteria.

The deployment of data prioritisation can enable the present invention's communication bandwidth to be preserved for the most crucial information during data communication limits. For example, a cardiac signal monitored at 512 bytes per-second may not be possible in some extreme remote monitoring conditions. However, remote medical diagnosis may still be possible as long as vital measures such as heart-rate remain uninterrupted. Moreover, 1 second updates of heart rate measures, along with alerts and event indications for arrhythmia or palpitation in circumstances such as irregular or missed heart beats, arrhythmias, or palpitations can in some situations provide adequate guidance to a remote medical monitoring site. Based on the local monitoring system analysing and detecting events as well as computing the heart rate measures, it is possible to maintain heart rate monitoring with a little as 1 update of the heart rate measure per second, representing a bandwidth reduction as much as 1/512.

Consequently, the present invention has the inherent intelligence and capability to manage these types of data reduction approaches, as well as implementing the deployment of backup communication techniques, in an orderly and deterministic manner, which is highly relevant to high-dependence or critical data connectivity management.

The Present Invention

Nub of Present High-Dependence Connectivity Monitoring (HDCM) Network Application Services [NAS] Invention with Data, Resource and NAS Connectivity Management and Prioritisation Capabilities for eHealth and Other Critical Monitoring Requirements The nub of the present apparatus/method invention is a mobile phone/computing device capable of monitoring and/ or working in conjunction with an embedded or separately integrated patient worn/attached and/or detached monitoring/sensor system(s) with optional integration to network application services (NAS), capable of dynamic (online) "adaptation" of system resources associated with one or more mobile devices or monitoring systems, monitoring conditions, interconnectivity conditions, interconnectivity resources and/or status or conditions associated with subject/object/environmental-aspect being monitored and applicable to high-dependence connectivity monitoring (HDCM) requirements, in accordance to data prioritisation and management requirements, whereby said HDCM system comprises any of:

- Whereby said "adaptation" can incorporate system parameters adjustment in order to optimise the said "mobile device" and associated monitoring devices or systems in a manner whereby the network application services (NAS) and other interconnectivity aspects, along with these device(s) or system resources (including but not limited to those listed under "Refer MONITORING SYSTEM CONFIGURATION per sections 1 to 6 herein) can be optimised to ensure critical data, warnings, alerts, requests for assistance or intervention and the like are prioritised in a manner to best mitigate risks and minimise delays, diagnostic ambiguity or loss of high-dependence (critical) data communications;
- Whereby said "adaptation" includes adaptation to IT/interconnectivity conditions;
- Whereby said "adaptation" includes adaptation to environmental or hazardous conditions;
- Whereby said "adaptation" and/or "system management" includes recognition and adaptation to the location of person or associated personal device (such as eHealthAtlas device or method described elsewhere in this document) based on (but not limited to) GPS or other locational system associated with a mobile device or user;
- Whereby said "adaptation" and/or "system management" includes adaptation to applicable monitoring requirements (such as but not limited to medical, IT/interconnectivity conditions, environmental conditions, monitoring requirements; hazard conditions);
- Whereby said "adaptation" and/or "system management" includes adaptation to (feedback/adjustment/optimisation) to required data prioritisation and/or interconnectivity status (delays, reliability etc.);
- Whereby said "adaptation" and/or "system management" includes mediation of higher data-bandwidth raw signals or associated data (such as monitored physiological signals or related measures or monitored environmental conditions or hazards or related signals or measures), versus lower-band-width data or measures (such as but not limited to system status, patient health status, system warnings, patient health condition warnings, summaries of primary data or primary data combinations such as (but not limited to) related indices, numeric, tabular and/or graphic summaries or measures trends, projected risks, crucial readings and the like), in accordance to prioritisation or importance of data interconnectivity (such as but not limited to health intervention alerts, critical health status alerts, measures, trends, projected risks, crucial readings and the like);
- Whereby adaptation" and/or "system management" and/or "high-reliability management" system, process, method, application or device of any hybrid combination of such parts continually monitors ongoing and projected (modelled/predicted) interconnectivity characteristics and compares these to the "minimally acceptable interconnectivity characteristics". The comparison to "minimally acceptable interconnectivity characteristics" includes (but is not limited to the current scope or maximum-capabilities of the interconnectivity characteristics versus the ongoing interconnectivity demand requirements, in order to predict and where appropriate mitigate, by way of early data management intervention, connectivity issues such as exceeding minimally acceptable interconnectivity characteristics;
- Whereby said "interconnectivity resources" can involve the allocation of available bandwidth of any available communication mediums (satellite network or links, cellular network or links, optical network or links, copper-network or links etc., microwave network or links etc.). For example, emergency beacon messages calling for external intervention, rescue, paramedics, or any other assistance could be allocated precedence to the general communication network or links where specialised services (i.e. eHealthNAS or GOeHealth services have been deployed). Similarly, remote monitoring of an aircraft's engine bearings where by vibration or wear signs indicate possible risk could similarly warrant a prioritised communication network or link capabilities.
- Whereby said "status or conditions" associated with subject/object/environmental-aspect (such as with eHealthATLAS per elsewhere herein) can refer to the prioritisation of data interconnectivity associated with the severity or importance of the monitored status or condition. For example, a hospital's emergency room (ER) or a rural regions connection to an ER eHealth-NAS monitoring application could allocate limited data bandwidth in accordance to vital sign warnings and indices versus data of secondary importance that otherwise may delay or compromise information transfer (i.e. increase risk to patient being remotely monitored and/or diagnosed).
- Additionally, the present invention enables data prioritisation system, whereby data acquisition, compression and other data management aspects can be dynamically adapted within predetermined criteria (parameter settings per ranges such as those in "MONITORING SYSTEM CONFIGURATION" per sections 1 to 6 herein), so that the present inventions data demands can be adapted to retain essential interconnectivity characteristics, regardless of changing environmental or interconnectivity conditions;
- Additionally, the present invention enables an integral (or independently located) data mirroring and/or buffering system, whereby data communications are mirrored and/or buffered in such a way that a backup system at all times ensures that critical data loss is avoided and system can seamlessly and automatically track problematic interconnectivity instances or periods with end-to end error message or warning alerts, while determining the fastest and most optimal strategy and restoration (or later assembly or data reconstitution/ alignment/synchronisation) for any inadvertent instances where minimally acceptable interconnectivity characteristics or preferred interconnectivity characteristics are compromised or trending (or predicted/modelled) towards potential compromise;

The present invention enables a failsafe "HDCM-watchdog", which can be integral to the mobile device or monitoring systems (and/or separately or independently located) and enables failsafe surveillance or tracking, together with warning and system status messages, as well as early warning or interventional countermeasures or backup interconnectivity measures to otherwise mitigate excessive risks or unacceptable circumstances. For example, the "HDCM-watchdog" system can trigger the access to secondary or emergency communication or computer system resources sync as (but not limited to) localised wireless or wire linked backup router systems or backup communication channels including (but not limited to satellite, optical or additional/supplementary/reinforced cell channels connections routing arrangements);

The present invention enables preferred (primary) interconnectivity characteristics but also has access to backup or secondary interconnectivity characteristics, systems or NAS such as (but not limited to) satellite, optical or additional/supplementary/reinforced cell channels connections routing arrangements;

The present invention enables a number of Interconnection mediums and formats Including (but not limited to) Cellular Carrier, Wi-Fi, Copper Bluetooth, Satellite, Optical Network, etc.;

The present invention enables data tracking, management and assurance in accordance to predetermined (and/or dynamically and/or online determined) levels of data integrity, data-throughput, data-bandwidth requirements, data bandwidth allocation and prioritisation, essential information (such as pre-defined crucial clinical measures) and "HDCM-watchdog backup" techniques designed to ensure fail-safe back-up intervention (such as ambulance or other healthcare services) as well as emergency alerts, alarms, and notifications (such as delays in vital sign measurement updates and the like);

The present invention enables automatic searching and finding of mobile monitoring system or sensors in order to automatically, or via user choice, configure and/or determine system monitoring format (i.e. HAS type 1, 2, 3, 4 or HBSS level 1, 2, 3) in order to intuitively adopt appropriate configurations and setting for system monitoring or diagnostic study type;

The present invention enables feedback control system via combined GPS user-location information (such as via eHealthATLAS application described herein) and localised conditions including those monitored conditions such as (but not limited to) environment, hazards and health status/risk including (but not limited to) asthma risks, allergy risks, pollen risks, pollution or smog risks etc., along with treatment or automatic control feedback such as activation or air-filters, warnings of asthma Ventolin requirements, breathing mask recommendations, earphone sleep recommendations etc.;

The present invention enables adaptation in accordance to data prioritisation, operational, functional, and network application services (NAS) requirements applicable to nature and type of monitoring application (including but not limited to eHealth, consumer, industrial and other monitoring applications);

HDCM-watchdog surveillance nub of the present invention: The HDCM-watchdog surveillance function is an monitoring system, application, data connectivity and/or communication management system which enables crucial healthcare diagnostic status or therapeutic control to be continuously overviewed in a "HDCM-watchdog" surveillance manner to ensure crucial healthcare-management functions and information prioritised to minimise or eliminate incidents which can lead to adverse eHealth outcomes.

The present invention optimises applications, connected devices and associated applications (including SAAS and/or Cloud and or Cloud-loaded devices, programs and other infrastructure) in accordance with pre-established and important standards or requirements (including pre-determined diagnostic, government reimbursement guidelines, standards or other medical, industrial or consumer standards, guidelines, codes or the like) applicable to medical monitoring, diagnostic or other industrial, consumer, or professional applications where minimal standards of monitoring, data interconnectivity, and/or levels of diagnostic validity are important;

The present invention optimises applications, connected devices and associated applications (including SAAS and/or Cloud and or Cloud-loaded devices, programs and other infrastructure) and/or medical or industrial therapy or treatment devices or systems (via open loop, feedback/phase-locked or a combination or other control techniques) in accordance with pre-established and important standards or requirements (including pre-determined diagnostic, government reimbursement guidelines, standards or other medical, industrial or consumer standards, guidelines, codes or the like) applicable to medical monitoring, diagnostic or other industrial, consumer, or professional applications where minimal standards of monitoring, data interconnectivity, and/or levels of diagnostic validity are important;

Monitoring or Mobile ICT System Configurations

1. Monitoring Device Configurations (Online; Offline; Local; Remote-Linked Site; Remote Monitoring Services/NAS)

Configuration requirements, adjustment criteria, optimisation criteria, and/or adaptation/feedback can be deployed in accordance to system operational requirements including (but not limited to) "monitoring system configuration", monitoring mobile phone/computer parameters, monitoring system view parameters, monitoring system review parameters, monitoring system storage parameters, across the complete range of system monitoring functions including (but not limited to) monitoring study format and associated monitored parameters, systems data responses, data interconnectivity, data buffering, data acquisition and preamplifier settings subject to system administrator roles with associated access levels, privacy and security requirements whereby said "monitoring system configuration" include (but are not limited to):

1.1 Monitoring Study Format (MSF) and Associated Monitored Parameters
   i. Government Health Insurance (USA; Australia; Germany; Japan)
   ii. USA Central Medical Service (CMS) type 1; 2; 3; 4
   iii. Australia Medicare Requirements level 1; 2; 3
1.2 Data Response (DR)
   iv. Data interconnect rates
   v. Data delays
   vi. Data delay variability
   vii. Data throughput/bandwidth viii. Data prioritisation
ix. Minimal emergency data configuration
x. Minimal deterministic data criteria
xi. Transducer Time Delay Factors
xii. Measurement System Time Delay Factors
xiii. Data Acquisition Time Delay Factors
xiv. Alarm, Warning and other Notification Time Delay Factors 1.3 Data Interconnectivity (DI)
i. Independent tracking/"HDCM-watchdog" function on/off and parameters
ii. Primary intercommunication channel(s) and/or medium(s) parameters
iii. Secondary intercommunication channel(s) and/or medium(s) parameters
iv. Interconnectivity data bandwidth channel allocation (a)
v. Interconnectivity medium type(s) and associated allocation (a)
vi. Interconnectivity bandwidth/throughput and associated allocation
vii. Interconnectivity data switching and/or data merging format(s) and associated allocation
viii. Interconnectivity data prioritisation and associated allocation
ix. Channel selection or montages
x. Interconnectivity data Compression
xi. Interconnectivity data Privacy
xii. Interconnectivity data Security
xiii. Minimal emergency data configuration
xiv. Minimal deterministic data criteria
xv. Data resolution
xvi. Data sampling rates
xvii. Data down-sampling and/or spline filtering or other data reduction techniques.

Notes a) can include (but not limited to) multiple data channels or multiple connections associated with any combination of *such as but not limited to optical, wireless, copper, other wire connect, electromagnetic, satellite linked cellular network, other network, Bluetooth wireless, Wi-Fi, direct data connection, satellite, cellular network and other interconnectivity options.

1.4 Data Buffer (DB)
i. Data buffer availability
ii. Data buffer allocation
iii. Data buffer prioritisation
iv. Data buffer usage
v. Minimal emergency data configuration
vi. Minimal deterministic data criteria 1.5 Data Acquisition (DA)
i. Channel selection or montages
ii. Data prioritisation
iii. Data down-sampling and/or spline filtering or other data reduction techniques.
iv. Data acquisition sample rate (i.e. 1, 2, 4, 8 . . . 4096, 5 kHz, 10 kHz, 20 kHz etc.)
v. Data acquisition filtering
vi. Data acquisition aliasing filter characteristics
vii. Data acquisition resolution (∧.e 8, 16, 22, 24 bit etc.)
viii. Data sampling rates
ix. Minimal emergency data configuration
x. Minimal deterministic data criteria 1.6 Signal Preamplifier (SP)
i. Channel selection or montages
ii. Filter types
iii. Filter characteristics
iv. Input sensitivity/gain
v. Impedance test settings
vi. Impedance test settings
vii. Signal quality surveillance settings
viii. Signal quality surveillance settings
ix. Automatic and/or manual signal issue tracking/diagnostic/correction/prevention
x. Stimulus
xi. Minimal emergency data configuration
xii. Minimal deterministic data criteria 2. Monitoring Mobile Phone/Computer Parameters (Online; Offline; Local; Remote-Linked Site; Remote Monitoring Services/NAS)
Per 1.1 to 1.6 above 3. Monitoring System View Parameters (Online; Offline; Local; Remote-Linked Site; Remote Monitoring Services/NAS)
Per 1.1 to 1.6 above 4. Monitoring System Review Parameters (Online; Offline; Local; Remote-Linked Site; Remote Monitoring Services/NAS)
Per 1.1 to 1.6 above 5. Monitoring Storage Parameters (Online; Offline; Local; Remote-Linked Site; Remote Monitoring Services/NAS)
Per 1.1 to 1.6 above 6. Administrator Roles (AR)
6.1 Standard (SAR)
i. User/Consumer
ii. Patient
6.2 Advanced (AAR)
i. Physician (GP; doctor) system administrator
ii. Referring physician system administrator
iii. Specialist system administrator
iv. Nurse system administrator
v. Medical co-ordinator system administrator
vi. Health-worker system administrator
vii. Scientist system administrator
viii. Technician system administrator
ix. IT system administrator
x. NAS system administrator
xi. Clinician system administrator
xii. Clinical Data system administrator
xiii. Home Health Care Provider system administrator
xiv. Health Insurance Provider system administrator
xv. Durable Medical Equipment (DME) Supplier system administrator
xvi. Health Medical Organisation (HMO) system administrator
xvii. Laboratory system administrator Whereby "parameters" and/or "monitoring system configuration" refers to (but is not limited to):
i. System Criteria
ii. System Data and/or process prioritisation criteria and/or requirements
iii. System Adaptation criteria and/or requirements
iv. Adjustability criteria and/or requirements
v. System stakeholder configuration libraries of settings, montages and/or other configurations criteria and/or requirements
vi. Minimum criteria and/or requirements
vii. Nominal criteria and/or requirements
viii. Actual criteria and/or requirements
ix. Projected/Modelled or predicted criteria and/or requirements (i.e. data bandwidth demand versus reliable base-bandwidth delivery or continuous data-bandwidth availability, along with system resource and/or interconnectivity availability versus usage at any point in time and predicted/projected future point in time)

x. Preferred/Optimal criteria and/or requirements
xi. Safe Operating Range criteria and/or requirements
xii. Safe Operating Mode criteria and/or requirements
xiii. Thresholds and/or limits criteria and/or requirements
xiv. Margins of Safe Operation Whereby system control and associated views are determined in accordance to "system stakeholder roles and associated access rights", "system security level requirements", and/or "system privacy level requirements" and/or "system stakeholder role".

Whereby said "monitoring system configuration" includes (but is not limited to) configuring minimum, nominal, and/or maximum values.

Example Embodiments

Physiological Data Monitoring Connectivity with High Dependence Connectivity Monitoring (HDCM) System The HDCM system manger provides the overall system management that tracks both minimally acceptable and preferred connectivity criteria against available data bandwidth/throughput, available data connectivity reliability. The purpose of the HDCMS system is to predict and avert connectivity issues or risks in advance and where avoidable data failures or performance issues are imminent to ensure the system users are presented with best available back-up processes and system notifications or warnings so that such instances can be accommodated in the context of patient safety. For example, clinicians or health workers must always be provided data latency or data alignment information to ensure that the time delays or readings of data including vital signed has been examined in advance in terms of minimally acceptable criteria and the recipients of this data or such measures require the confidence that the data has been pre-screened and validated in terms of crucial factors such as data response delays, lost or missing data segments, data response variations, synchronisation between data channels or information mediums such as diagnostic physiological, video and/or audio information. i.e. electrocardiogram, blood pressure and heart rate readings need to be updated at regular and minimal time intervals, must have minimal and predefined delays between a user/patient being monitored and the reception of such information, and the stability and status of these factors must be both available for the system users as well as linked to alarms. The present invention's acceptable levels of operation and associated alerts or alarms can be configured as configured and/or approved by the appropriate and designated responsible clinical systems ICT manager/group (the said "configured" and/or "approved" responsible clinical systems ICT manager/group is usually comprise of the health workers guided by the eHealth NAS services provider to ensure safe and appropriate guidelines and/or regulatory standards are heeded in order to minimise eHealth risks.

Dynamic Track and Data Adaptation Function During Critical Data Monitoring Application The present invention is capable of deploying an independent interconnectivity status surveillance system ("HDCM-watchdog" type approach), whereby the crucial interconnectivity characteristic of the communication systems are continuously monitored in order to identify, and where possible and appropriate, pre-empt and avert interconnectivity issues or risks. In the above example, where the timing characteristics associated with monitoring an individual's cardiac function can be crucial to a remotely located clinician, the CriticalData Communication Status can enable (for example but not limited to) in one of the simplest context a green indicator "OK" status indication or red indicator "NO" interconnectivity status for both the local and remotely connected sites. This status would be configured in accordance to the available connectivity circumstances (available communication methods and networks as well as band data interconnectivity aspects such as reliability and bandwidth availability, as well as data demand factors such as the application bandwidth requirements, user-interface application criteria, and data prioritisation factors). The present invention continuously tracks essential data interconnectivity characteristics and compares said characteristics to predetermined minimal data interconnectivity criteria in order to detect data communication issues (such as data integrity, lost data packets etc.) and data demands (such as but not limited to data throughput and data bandwidth, data delay, delay variances etc.) in comparison to predetermined data interconnectivity requirements (such as but not limited to) to enable measures and countermeasures capable of detect said communication issues. Additionally, the HDCM system incorporates the ability to indicate, alert or notify users at the various locations during any interconnectivity session, as to the status or critical factors associated with the status (such as bot not limited to any of MONITORING SYSTEM CONFIGURATION per sections 1 to 6 parameters/criteria) relating to whether or not the interconnectivity associated with a remote monitoring communication session is operating within pre-detrained requirements, limits and minimum acceptable criteria, as well as indicate enough information to help mitigate the potential false sense of user security or misleading data interpretations which could otherwise exist.

Cardiac Monitoring Example

In one embodiment of the present invention, a user can deploy a connected eHealth (mHealth) cardiac monitoring system. In circumstances where the primary connection method (such as the mobile cellular network) is confronted with mobile device communication constraints during periods (for example only) of excessive cell-network load or during periods of poor communication reception, the present invention can ensure local heart rate alerts and remote monitoring alerts (i.e. 24 hour health-care surveillance centres) remain actively updated and connected at all times. Similarly, the present invention can automatically and seamlessly invoke secondary or backup communication channels such as satellite data connections to ensure real-time monitoring remains uninterrupted during more important monitoring applications. In circumstances where less critical monitoring application is deployed and back-up or secondary intercommunication measures (such as "HDCM-watchdog" systems or functions described elsewhere herein) are not warranted, the user may be alerted that delays in data monitoring are currently being experienced, along with the range and average data delay times (for example but not limited to).

Example of Mobile Device HDCM Embodiment

In one embodiment of the present invention one or more bar-graphs can be colour-coded (for example, red for emergency data channel, orange for desirable data channel data, and green for optional data channel, etc.) and assigned in accordance to data prioritisation relating to the different communication mediums available in the specific connection scenario (i.e. emergency SMS data, cellular data, back-up satellite link, mobile emergency beacon or medical pager intervention alert, local HDCM-watchdog system etc.).

In this way the duly authorised HDCM system administrator can appropriately allocate primary interconnectivity, secondary interconnectivity, and fail-safe interconnectivity, as well as emergency beacon interconnectivity formats with immediate bandwidth demand, bandwidth requirement, and data prioritisation management system visibility. Moreover, this management system can be view online via HDCM system interconnectivity management service as well as the same or separate HDCM system remote monitoring and medical intervention service should these options be required by the system users.

Importantly, the HDCM system can be designed to locally buffer or record all data and then enable this data to be seamlessly reconstituted at a later time in the form of a continuous, uninterrupted record, regardless of interconnectivity conditions experienced during the original monitoring session.

Additionally the present invention can enable a simplified user interface view of a range of monitored vital signs, with a means of enabling bandwidth allocation comprising of low-bandwidth data allocations for critical vital signs numeric measures.

These critical measures can be assigned as "high-data-priority" information for numeric, tabular and/or graphically displayed indices. Less critical information can be assigned as "low-data-priority" information (such as optional video data, for example). Moderately important information such as raw physiological data, which can be uploaded at a later time, can be assigned "medium-data-priority" status.

In this way various monitored channels or raw data or derived measures and indices can be assigned various levels or data priority, so that this hierarchy can be acknowledged during compromised communication periods to avoid loss of critical information exchange.

Additionally, each data channel or derived measure can be assigned to primary, secondary and emergency or "HDCM-watchdog" communication channels or mediums.

Each monitoring data channel can be configured in order to define acceptable limits for medical information latencies (system responsiveness), stability or latencies (variances and variability of time delays) and alignment (synchronisation) between different channels of data or data types (such as video, audio, signals etc.)

LIST OF FIGURES

FIG. 1: Example of Mobile application/system incorporating High Dependence Connectivity Monitoring (HDCM) System incorporating Adaptive Network Application Services (NAS) with integrated management and dynamically configurable and adjustable resources (Modes, Functionality, Access, Interconnectivity, and Data Prioritisation) of one or more monitoring devices and/or mobile systems.

FIG. 2: Example of Mobile application/system user interface incorporating High Dependence Connectivity Monitoring (HDCM) System incorporating Adaptive Network Application Services (NAS) with integrated management and dynamically configurable and adjustable resources (Modes, Functionality, Access, Interconnectivity, and Data Prioritisation) of one or more monitoring devices and/or mobile systems.

FIG. 3: Dynamically adaptive high-dependence connectivity management system (HDCMS) for deterministic data interchange block diagram overview FIG. 4. Dynamically adaptive high-dependence connectivity management (DAHD) system.

FIG. 5. Online mobile-monitoring map-linked health-tracking including integral environment and hazard monitoring & environment conditions.

FIG. 6. Health-linked navigational aids—i.e. routing travel with sensitivity to asthmatic risk zones of excessive pollution, pollen or allergy alerts, as shown here.

FIG. 7A. depicts a schematic diagram illustrating attributes available for eHeathAtlas control configuration, user/patient information history, and other reporting and monitoring attributes.

FIG. 7B. depicts a schematic diagram illustrating health report information, status, settings, alerts, and other reporting and monitoring attributes.

FIG. 8. depicts a schematic diagram illustrating Software as a Service (SaaS) and Application Services (NAS) interfaces.

Figure 1:
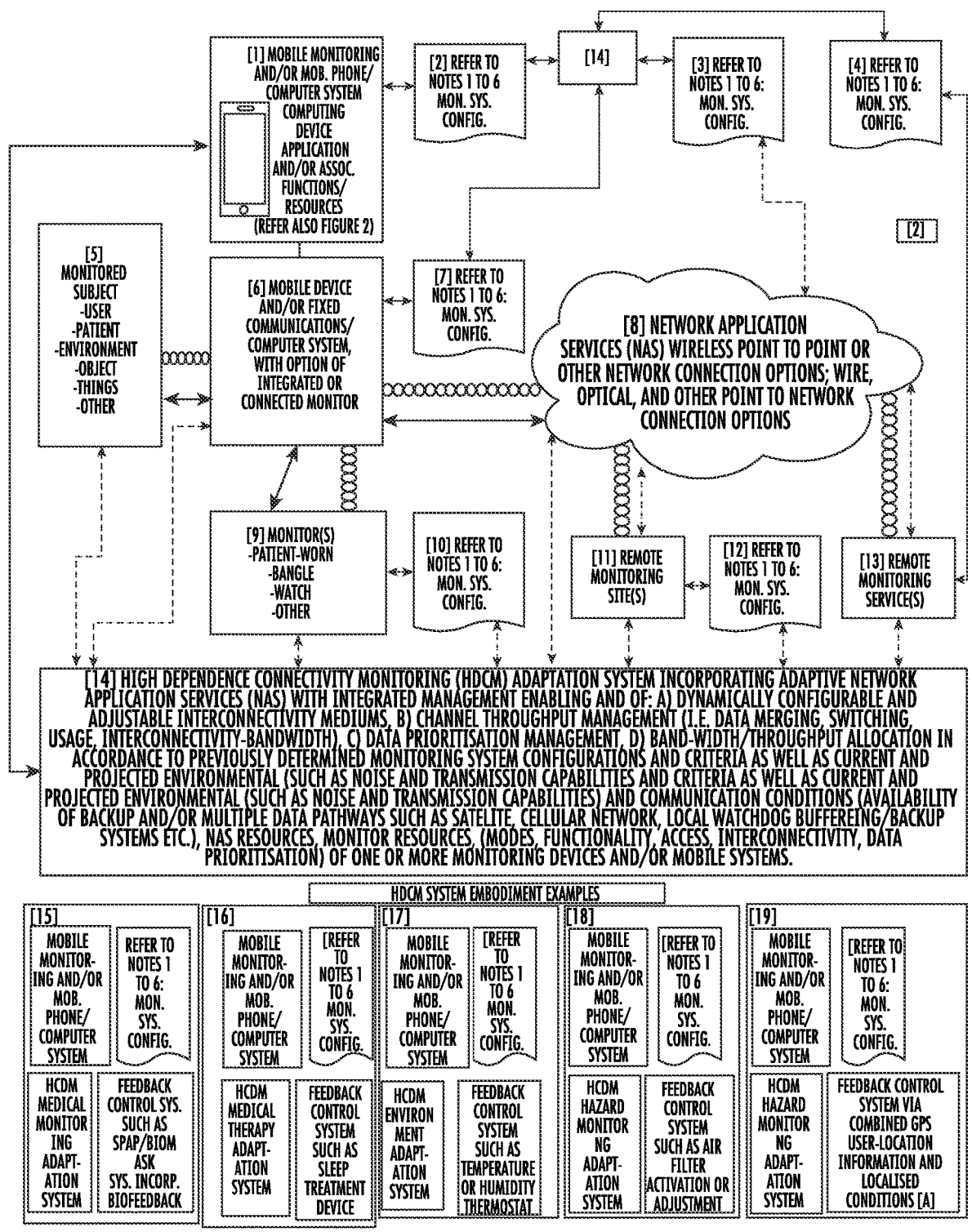
FIG. 1:
Example of Mobile application/system incorporating High Dependence Connectivity Monitoring (HDCM) System incorporating Adaptive Network Application Services (NAS) with integrated management and dynamically configurable and adjustable resources (Modes, Functionality, Access, Interconnectivity, Data Prioritisation) of one or more monitoring devices and/or mobile systems.

[1] Mobile monitoring and/or mob. phone/computer system Computing Device Application and/or assoc. functions/resources (refer also FIG. 2)
[2] Refer to notes 1 to 6: Mon. Sys. Config.
[3] Refer to notes 1 to 6: Mon. Sys. Config.
[4] Refer to notes 1 to 6: Mon. Sys. Config.
[5] Monitored Subject
User
Patient
Environment
Object
things
other
[6] Mobile Device and/or fixed Communications/Computer system, with option of integrated or connected monitor
[7] Refer to notes 1 to 6: Mon. Sys. Config.
[8] Network Application Services (NAS) Wireless point to point or other network connection options; wire, optical, and other point to point or network connection options
[9] Monitor(s)
Patient-worn
Bangle
Watch
other
[10] Refer to notes 1 to 6: Mon. Sys. Config.
[11] Remote Monitoring Site(s)
[12] Refer to notes 1 to 6: Mon. Sys. Config.
[13] Remote Monitoring Service(s)
[14] High Dependence Connectivity Monitoring (HDCM) Adaptation System incorporating Adaptive Network Application Services (NAS) with integrated management enabling any of: a) dynamically configurable and adjustable interconnectivity mediums, b) channel throughput management (i.e. data merging, switching, usage, interconnectivity-bandwidth), c) data prioritisation management, d) bandwidth/throughput allocation in accordance to previously determined monitoring system configurations and criteria as well as current and projected environmental (such as noise and transmission capabilities) and communication conditions (availability of backup and/or multiple data pathways such as satellite, cellular network, local HDCM-watchdog buffering/backup systems etc.), NAS resources, monitor resources, (Modes, Functionality, Access, Interconnectivity, Data Prioritisation) of one or more monitoring devices and/or mobile systems.

[15]
Mobile monitoring and/or mobile phone/computer system
Refer to notes 1 to 6: Monitoring System Configuration
HCDM Medical Monitoring Adaptation System
Feedback control system such as SPAP/biomask system incorporating biofeedback

[16]
Mobile monitoring and/or mobile phone/computer system
Refer to notes 1 to 6: Monitoring System Configuration
HCDM Medical therapy Adaptation System
Feedback control system such as sleep treatment device

[17]
Mobile monitoring and/or mobile phone/computer system
Refer to notes 1 to 6: Monitoring System Configuration
HCDM Environment Adaptation System
Feedback control system such as temperature or humidity thermostat

[18]
Mobile monitoring and/or mobile phone/computer system
Refer to notes 1 to 6: Monitoring System Configuration
HCDM Hazard Monitoring Adaptation System
Feedback control system such as air filter activation or adjustment

[19]
Mobile monitoring and/or mobile phone/computer system
Refer to notes 1 to 6: Monitoring System Configuration
HCDM Hazard Monitoring Adaptation System
Feedback control system via combined GPS user-location information and localised conditions [a]

[a] (including those monitored conditions such as (but not limited to) environment, hazards and health status/risk including (but not limited to) asthma risks, allergy risks, pollen risks, pollution or smog risks etc., along with treatment or automatic control feedback such as activation of air-filters, warnings of asthma Ventolin requirements, breathing mask recommendations, earphone sleep recommendations etc.

Figure 2:
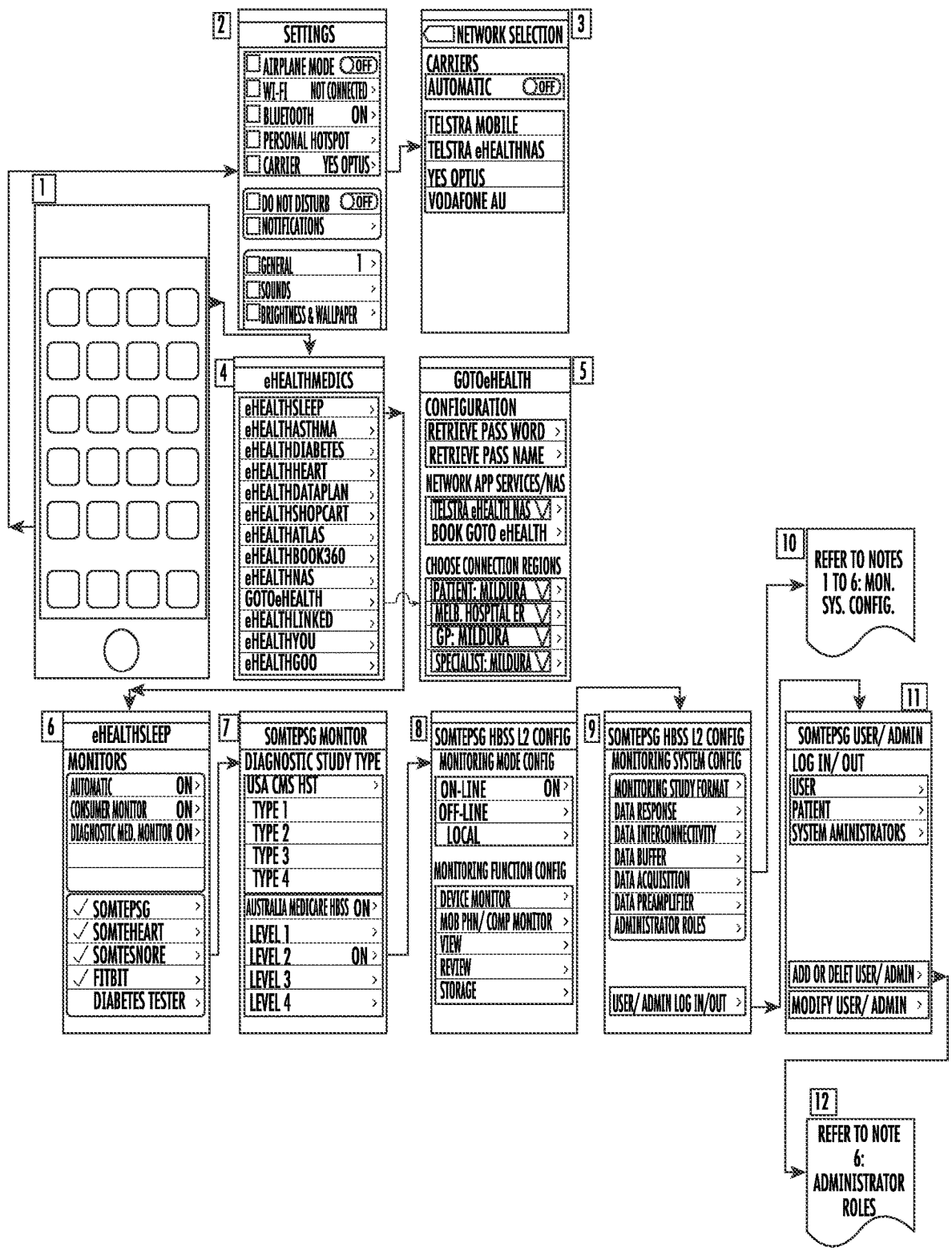

FIG. 2:
Example of Mobile application/system user interface incorporating High Dependence Connectivity Monitoring (HDCM) System incorporating Adaptive Network Application Services (NAS) with integrated management and dynamically configurable and adjustable resources (Modes, Functionality, Access, Interconnectivity, Data Prioritisation) of one or more monitoring devices and/or mobile systems.

Figure 3:
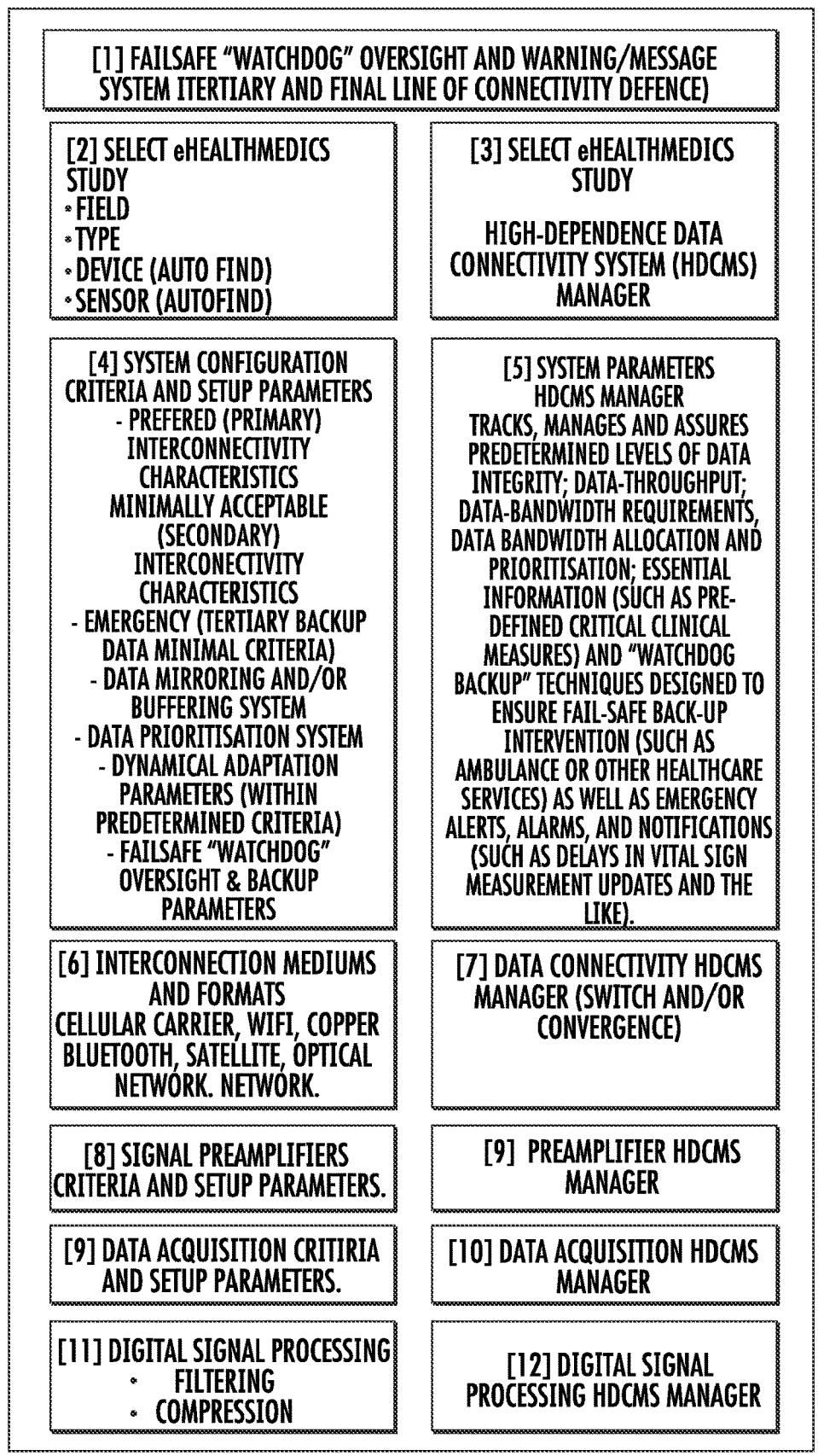
Figure 4:
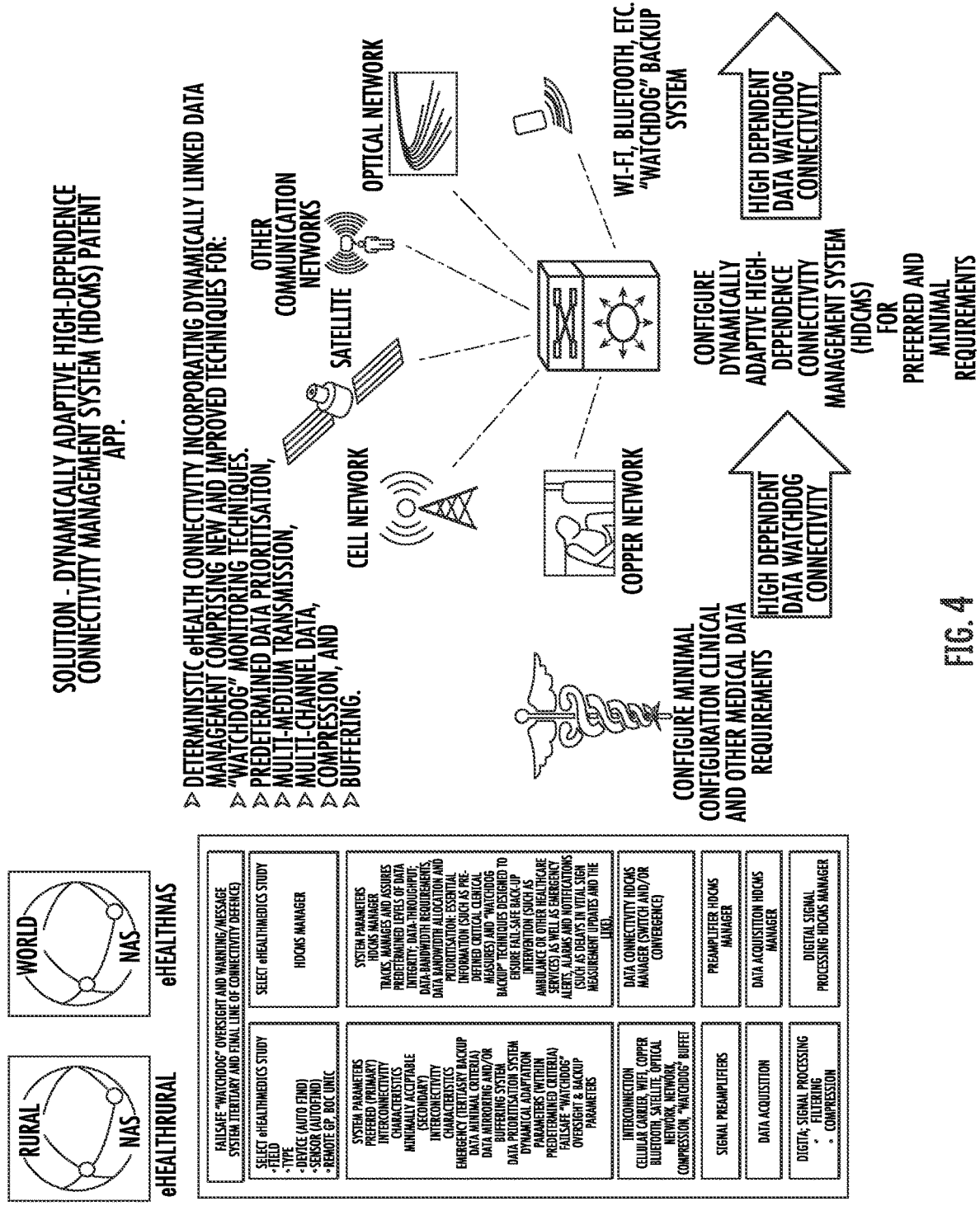
Figure 5:
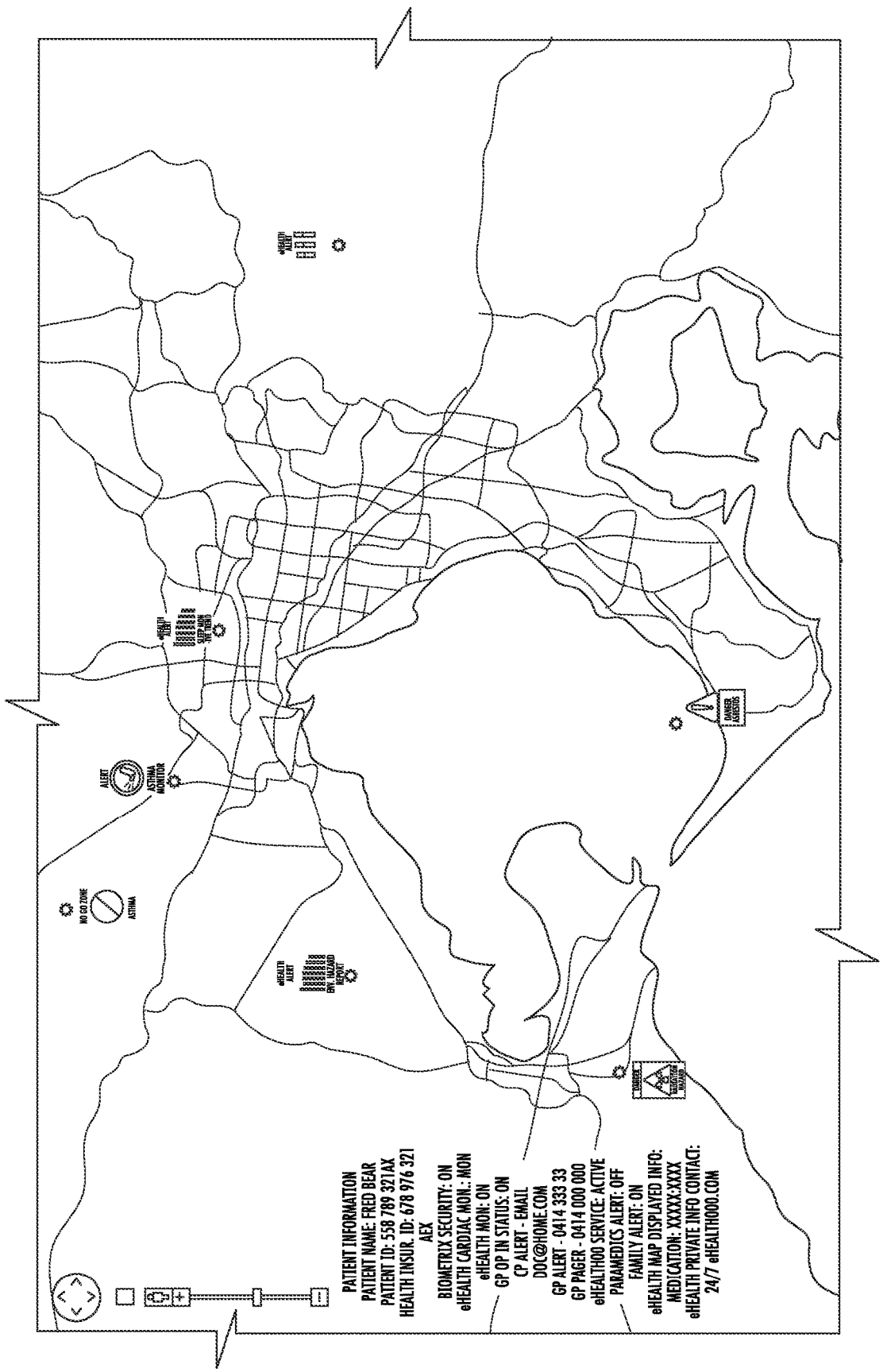
Figure 7A:
Figure 8:
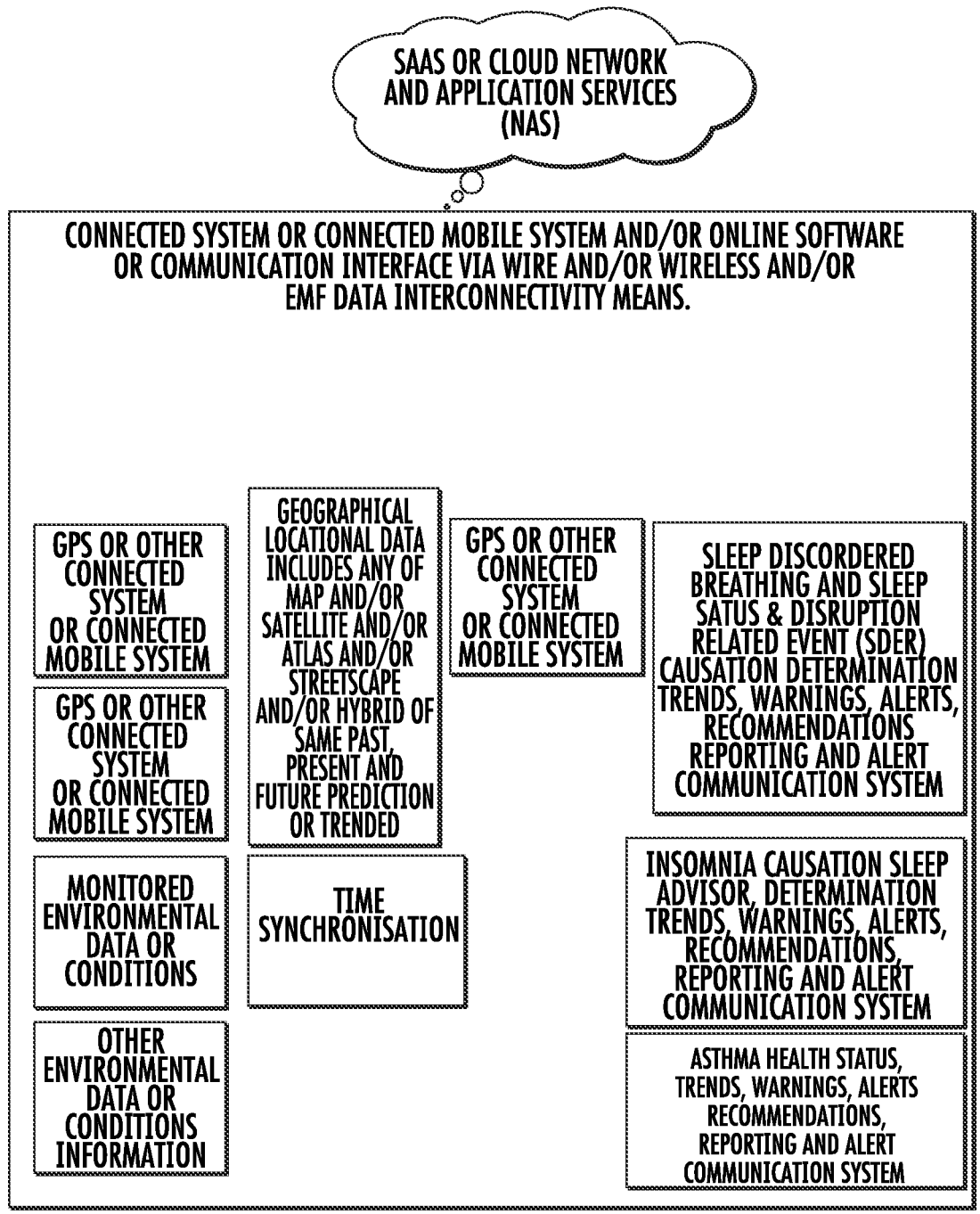

FIG. 3:
Dynamically adaptive high-dependence connectivity management system (HDCMS) for deterministic data interchange block diagram overview
[1] FAILSAFE "WATCHDOG" OVERSIGHT AND WARNING/MESSAGE SYSTEM (TERTIARY AND FINAL LINE OF CONNECTIVITY DEFENCE)
[2] SELECT eHealthMedics STUDY
FIELD
TYPE
DEVICE (AUTO FIND)
SENSOR (AUTOFIND)
[3] SELECT eHealthMedics STUDY
High-Dependence Data Connectivity System (HDCMS) Manager
[4] System Configuration Criteria and Setup Parameters
PREFERRED (PRIMARY) INTERCONNECTIVITY CHARACTERISTICS
MINIMALLY ACCEPTABLE (SECONDARY) INTERCONECTIVITY CHARACTERISTICS
EMERGENCY (TERTIARY BACKUP DATA MINIMAL CRITERIA)
DATA MIRRORING AND/OR BUFFERING SYSTEM
DATA PRIORITISATION SYSTEM—DYNAMICAL ADAPTATION PARAMETERS (WITHIN PREDETERMINED CRITERIA)
FAILSAFE "WATCHDOG" OVERSIGHT & BACKUP PARAMETERS
[5] System Parameters
HDCMS Manager
Tracks, manages and assures predetermined levels of data integrity; data-throughput; data-bandwidth requirements, data bandwidth allocation and prioritisation; essential information (such as pre-defined crucial clinical measures) and "watchdog backup" techniques designed to ensure fail-safe back-up intervention (such as ambulance or other healthcare services) as well as emergency alerts, alarms, and notifications (such as delays in vital sign measurement updates and the like).
[6] Interconnection Mediums and Formats
Cellular Carrier, Wi-Fi, Copper Bluetooth, Satellite, Optical Network, Network,
[7] Data Connectivity HDCMS Manager (switch and/or convergence)
[8] Signal Preamplifiers criteria and setup parameters.
[9] Preamplifier HDCMS Manager
[10] Data Acquisition HDCMS Manager
[11] Digital Signal Processing
Filtering
Compression
[12] Digital Signal Processing HDCMS Manager
FIG. 4:
Dynamically adaptive high-dependence connectivity management (DAHD) system
FIG. 5:
Online mobile-monitoring map-linked health-tracking including integral environment and hazard monitoring & environment conditions
FIG. 6:
Health-linked navigational aids—i.e. routing travel with sensitivity to asthmatic risk zones of excessive pollution, pollen or allergy alerts, as shown here:
FIG. 7A: (per attached figure)
FIG. 7B: (per attached figure)
FIG. 8: (per attached figure)

The invention claimed is:
1. A system for monitoring and diagnosing data acquired and transmitted through multiple interconnected data channels, the data being sensor data acquired from physiological processes associated with the health condition or health status of the subject of monitoring and diagnosis, or sensor data acquired from environmental processes associated with the subject's environment, the system comprising:
a means to transmit acquired sensor data in one or more channels according to the data type that is the type of the sensor data; and
a computer processor or interconnected computer processors in communication with each other, wherein the computer processor incorporates a program to dynamically acquire the data from the sensor, adapt the data, monitor, view, review, analyze the data from said sensors, and to dynamically adapt the data transmission in real time on of one or more communication channels; and further to process the program configuration parameters online in real time and prioritize the transmitted data to keep the priority data connected during bandwidth limiting conditions, and further to process the program configuration parameters online in real time and prioritize the transmitted data to keep the priority data connected during bandwidth limiting conditions, and to acquire predetermined parameters associated with time synchronization between the data channels, or distortion differences, or data delay variability from the sensor data, and wherein the computer processor incorporates configuration parameters of the program, and monitors the data, views, reviews, analyzes, and prioritizes the process, and wherein the computer processor prioritizes a combination of sensor data acquired from the physiological process of the subject and sensor data acquired from an environmental process online in real time to optimize data transfer at all times, even during communication constraints in order to correlate the monitoring parameters and the communication parameters with each other and optimize system resources online in real time.

2. The system according to claim 1 wherein the data type includes video, audio, or imaging data.

3. The system according to claim 1 wherein the data is acquired from sensors monitoring an industrial process.

4. The system according to claim 1 where the data is acquired from remote sensors.

5. The system according to claim 1 wherein location information is monitored.

6. The system according to claim 1 wherein weather information is monitored.

7. A method for monitoring and diagnosing, the method comprising the steps of:
  (a) providing a system according to claim 1; and
  (b) processing monitoring, viewing, reviewing and analyzing the sensor data in accordance with the priority in said system, wherein the sensor acquires sensor data and the acquired sensor data is transmitted by the transmission means on a plurality of the data channels according to the data type.

8. The method according to claim 7, wherein the communication data or monitored data or process information is prioritizing, monitoring, viewing, reviewing, and analyzing constantly to address the most important interconnectivity.

* * * * *